United States Patent [19]

Kornberg et al.

[11] Patent Number: 5,243,109
[45] Date of Patent: Sep. 7, 1993

[54] TRIBROMOSTYRENE PRODUCTS AND PROCESS FOR MAKING THEM

[75] Inventors: Nurit Kornberg, Lehavim; David Beneish, Omer; Michael Peled, Beer-Sheva, all of Israel

[73] Assignee: Bromine Compounds Ltd., Beer-Sheva, Israel

[21] Appl. No.: 926,475

[22] Filed: Aug. 6, 1992

[30] Foreign Application Priority Data

Aug. 8, 1991 [IL] Israel ............................. 99130

[51] Int. Cl.$^5$ ..................... C07C 17/24; C07C 25/00
[52] U.S. Cl. .................................. 570/193; 570/189; 570/206; 570/216
[58] Field of Search ............. 570/193, 216, 219, 220, 570/206, 189

[56] References Cited

U.S. PATENT DOCUMENTS

| | | | |
|---|---|---|---|
| 4,292,453 | 9/1981 | Daren | 570/193 |
| 4,343,956 | 8/1982 | Jackisch | 570/105 |
| 4,423,262 | 12/1983 | Jackisch | 570/193 |
| 4,633,026 | 12/1986 | Kolich | 570/200 |
| 4,748,286 | 5/1988 | Daren | 570/200 |

FOREIGN PATENT DOCUMENTS 254305 1/1988 European Pat. Off. .
3337223 5/1985 Fed. Rep. of Germany .

*Primary Examiner*—Werren B. Lone
*Attorney, Agent, or Firm*—Michael N. Meller

[57] ABSTRACT

Tribromostyrene (TBS) is produced by the preparation of a TBS precursor, which is β-bromoethyl-tribromobenzene (β-BrBr$_3$), and the successive elimination of hydrogen bromide from said precursor. The precursor is prepared by selective bromination of phenethyl bromide (β-Br), wherein the molar ratio of bromine to phenethyl bromide is comprised between 2.5 and 3.5, and preferably between 3.1 and 3.3 included; and by adding bromine, after an initial addition, at a controlled molar rate.

16 Claims, No Drawings

TRIBROMOSTYRENE PRODUCTS AND PROCESS FOR MAKING THEM

FIELD OF THE INVENTION

This invention relates to improved tribromostyrene products and to a process for making them. More particularly, it relates to products which have high melting points and correspondingly long shelf lives, and comprise at least 90% by weight of tribromostyrene, and preferably more. The invention further relates to a process for the preparation, through the ring bromination of phenethyl bromide, of a tribromostyrene precursor of high purity, to a process for preparing said tribromostyrene products by preparing said precursor and removing hydrogen bromide therefrom.

THE PRIOR ART

Tribromostyrene is used as a flame retardant, optionally in combination with other flame retardants, for polymers having styrene as part of their molecular structure, such as polystyrene, styrene-butadiene copolymers, ABS, etc. Substitution in the molecules of such polymers of an amount of styrene units by ring halogenated styrene imparts satisfactory flame retardancy to the resulting copolymers.

In this specification, the word "tribromostyrene" (briefly indicated as TBS) includes mixtures of isomers, in particular isomers which are brominated at the 2,4,5 or at the 2,4,6 positions of the benzene ring. The particular proportions in which the isomers are present in the product are irrelevant as far as this invention is concerned, and will not be taken into consideration.

It is known in the art to prepare TBS by firstly preparing a precursor which is $\beta$-bromoethyl-tribromobenzene, and subsequently removing hydrogen bromide from the precursor by reaction with an alkali metal hydroxide in a two-phase system, comprising an aqueous phase and an organic solvent phase, in the presence of a phase transfer catalyst. Such processes are described, e.g., in U.S. Pat. Nos. 4,292,453 and 4,748,286. It is known to prepare the precursor by brominating $\beta$-bromoethylbenzene with bromine in the presence of an iron catalyst. Such a preparation is described, e.g., in the cited U.S. Pat. No. 4,748,286. The $\beta$-bromoethyl-tribromobenzene product thus obtained includes tribrominated isomers 2,4,5 and 2,4,6, as well as compounds having a degree of bromination different from 3, which will result in corresponding mixtures in the TBS finally obtained.

TBS tends to polymerize at relatively low temperatures and this shortens its shelf life and constitutes a serious drawback in the industrial use of the product. In order to limit this tendency to polymerize, it is suggested, e.g. in cited U.S. Pat. No. 4,292,453, to remove the catalyst used for converting the precursor to TBS. Nevertheless, the TBS products obtained according to the prior art have low melting points, resulting in inadequate shelf life, as they tend to polymerize relatively quickly at relatively low temperatures. The applicant has ascertained that this is due to the presence in the product of substantial amounts of secondary products, prevalently constituted by brominated styrenes having a degree of bromination different from 3, in particular dibromostyrene (hereinafter "DBS") and tetrabromostyrene (hereinafter "TeBS"). The presence of said secondary products, in turn, derives from the corresponding secondary products—particularly $\beta$-bromoethyl-dibromobenzene and $\beta$-bromoethyl-tetrabromobenzene—in the precursor. Actually, the art does not disclose truly specific bromination processes of this type of compounds. Even DBS cannot be prepared, according to the art, with high purity: see e.g. U.S. Pat. Nos. 4,276,186 and 4,633,026 and European Patent 291950. This is particularly true for the preparation of TBS. Thus, the precursor as described in cited U.S. Pat. No. 4,748,286 comprises 5% of $\beta$-bromoethyl-dibromobenzene (hereinafter $\beta$-BrBr$_2$) and 5% of $\beta$-bromoethyl-tetrabromobenzene (hereinafter $\beta$-BrBr$_4$), which give rise respectively to DBS and TeBS in the final product, and therefore to such a product which has low melting points. Thus dehydrobromination in ethanol (Example 4 of said U.S. Pat. No. 4,748,286) produces a TBS product having a melting point of 55° C. and dehydrobromination in isopropanol produces a TBS product which requires crystallization from n-hexane to reach a melting point of 64° C. (Example 1). The art does not provide extensive information relative to the effects of such impurities. Actually, it has been stated (U.S. Pat. No. 4,343,956) that DBS is more stable than TBS, while no particular influence is attributed in the art to the presence of TeBS. While it is possible to eliminate part of these impurities by purification, such procedures, if they become extensive, are expensive and industrially disadvantageous.

It is a purpose of this invention to provide TBS products which have a high shelf life and exhibit a reduced tendency to polymerize spontaneously.

It is another object of the invention to provide such TBS products in which the amount of TBS is at least 90%. All the percentages in this application are by weight, unless otherwise specified.

It is a further purpose of this invention to provide a process for preparing the aforesaid TBS products by the preparation of a precursor which, as prepared and before purification, is an at least 89% pure $\beta$-bromoethyl-tribromobenzene and contains less than 5% of $\beta$-BrBr$_2$, and subsequent elimination of hydrogen bromide from the precursor.

It is a still further purpose of the invention to provide a process for preparing such TBS products without carrying out extensive purification steps to eliminate impurities, and in particular DBS and TeBS and/or their precursors.

SUMMARY OF THE INVENTION

The aforesaid purposes are achieved by the preparation of a TBS precursor, which is $\beta$-bromoethyl-tribromobenzene ($\beta$-BrBr$_3$), by selective bromination of phenethyl bromide and the successive elimination of hydrogen bromide from said precursor. The said selective bromination process comprises reacting phenethyl bromide with bromine in the presence of a bromination catalyst, and is characterized in that:

(a) the molar ratio of Br$_2$ to phenethyl bromide is comprised between 2.5 and 3.5, and preferably between 3.1 and 3.3 included;

(b) at least after an amount of bromine comprised between 2 and 3, and preferably between 2.5 and 2.7 moles Br$_2$ per mole of phenethyl bromide has been added, the remaining bromine is added at a controlled molar rate that is not substantially greater than stoichiometrically equivalent to the molar rate of evolution of the hydrogen bromide, and preferably is substantially comprised between 80% and 100% of the stoichiometric amount;

(c) preferably, an halogenated solvent, non-reactive under the reaction conditions, is added to the reaction mass, in an amount of at least 0.5 ml per 3 grs of phenethyl bromide, preferably from about the beginning of the bromine addition control under (b); and (d) preferably, the bromine is uniformly dispersed throughout the reaction mass, at least from about the beginning of the bromine addition control under (b).

DETAILED DESCRIPTION OF PREFERRED EMBODIMENTS

The halogenated organic solvent used is chosen among solvents that are known in the art to be usable in bromination processes. Suitable examples are methylene chloride (MC), dibromomethane, 1,2-dichloroethane (EDC), 1,2-dibromoethane (EDB) CCl$_4$, 1,1,2-trichloroethane, etc. The solvent used is generally already effective at an amount of about 0.5 ml per 1 gr of phenethyl bromide ($\beta$-Br), but larger amounts may be desirable, although no improvement is usually detected when such amounts exceed 0.5 ml per gr of phenethyl bromide. The reaction time may vary widely and is determined by the bromine addition control, since times that would not be required by kinetic reasons may be needed in order to add all the required bromine at the rate determined by the rate of evolution of the HBr, according to the invention. E.g., it may be as low as 90 minutes or as high as several hours, e.g. 24 hours or more. Preferably the phenethyl bromide used should not contain more than 300 ppm of moisture, and if its content is higher, it should be dried, e.g. by addition of MC and evaporation thereof, whereby the moisture is entrained by it.

As stated above, it is desirable to disperse the bromine uniformly through the reaction mass, particularly from the moment at which the bromine addition control begins. This can be done by any suitable means. Stirring is a convenient such means, and its intensity can be easily decided in each instance by skilled persons. Additionally or alternatively, when the reaction is carried out under reflux the bromine can be added to the reflux vapours. Also, the bromine can be fed by fractional amounts at several points of the reaction mass. Other dispersing and uniforming means are known in the art. Two or more of the aforesaid and other means can be used concurrently.

The temperature throughout the reaction should be close to room temperature, e.g. 30° to 40° C. or to the reflux temperature, when the reaction is carried out under reflux and this latter controls the temperature. Since the reaction is strongly exothermic, the rate of addition of the bromine strongly influences the temperature, and if it is too rapid for the temperature to remain at the desired level, cooling may be necessary to maintain it. This should be taken into account in adding the bromine, even before its rate of addition is to be controlled according to the invention.

At the end of the reaction, if any unreacted bromine is present, it is neutralized with sodium bisulfite solution, the product is washed to eliminate residues of the catalyst and the solvent is evaporated.

The precursor thus obtained is dehydrobrominated to yield TBS by processes known in the art, e.g. from U.S. Pat. Nos. 4,292,453 and 4,748,286.

EXAMPLE 1

Preparation of $\beta$-BrBr$_3$

Into a 1-liter, 4-necked reactor, equipped with a mechanical stirrer, condenser, dropping funnel and thermometer, 0.6 moles of phenethyl bromide (111 grams), having a moisture content of 100 ppm, are charged, 1.5 gr of iron catalyst are added, and then 0.06 moles of bromine are added slowly at room temperature and the mass is stirred until hydrogen bromide begins to evolve. Thereafter, the temperature is adjusted and maintained at 40° C. and bromine is added at such a rate that the evolution of HBr is stable. When the total bromine added has reached 1.6 moles (about 2.7 moles per mole of $\beta$-Br), MC is added in an amount of 1 ml per gr of phenethyl bromide used, viz. 110 ml. The addition of bromine is continued, but at a rate that is substantially stoichiometrically equivalent to the HBr evolved, viz. in this example, between 0.2 and 0.5 grs per minute, until the total bromine added has reached 3.2 moles per mole of phenethyl bromide. The MC is refluxed, whereby the temperature is maintained at 36° C. The entire reaction lasts 210 minutes. At the end of this time, the reaction mass is treated with a sodium bisulfite solution, to neutralize any unreacted bromine, the product is washed twice with an aqueous HCl solution to eliminate residues of the iron catalyst, and the solvent is evaporated.

The product thus obtained is in an amount of 250 gr and consists of 91.4% of $\beta$-BrBr$_3$, tribromobenzene, 3.9% of $\beta$-BrBr$_2$ and 4.2% of $\beta$BrBr$_4$. It is pure enough to be passed directly to the dehydrobromination stage.

EXAMPLE 2

Preparation of TBS from $\beta$-BrBr$_3$

50 Gr. (0.12 moles) $\beta$-BrBr$_3$ dissolved in 25 ml MC also containing 0.4 gr. of a 64% aqueous solution of triethylbutyl ammonium bromide is stirred at room temperature, together with 0.5 gr. of sodium nitrite, and 47.5 gr. of 50% aqueous NaOH solution are then added. The mixture is stirred at 30° C. for 3 hours. Two phases, aqueous and organic, are formed and are separated, and the organic phase is washed with dilute acid to pH 5. The resulting solution is cooled down and filtered. The filtered product is in the amount of 33 gr. and contains 94% TBS, 5% TeBs and 1% DBS. Its melting point is 60°-64° C. The fact that such a pure product is obtained directly from the reaction, without any purification stages, is all the more surprising since the art (U.S. Pat. No. 4,748,286) teaches that the use of MC should have been harmful in view of its solvent properties.

EXAMPLE 3

Preparation of $\beta$-BrBr$_3$ and of TBS

The operations of Example 1 are repeated, with the following differences: the reaction lasts 250 minutes, the total amount of bromine is 3.3 moles per mole of phenethyl bromide, and the amount of MC used is 0.54 ml per gr of phenethyl bromide. The product obtained contains 91.9% of $\beta$-Br-Br$_3$, 1.3% of $\beta$-BrBr$_2$ and 6.6 of $\beta$-BrBr$_4$. It is treated as in Example 2 to furnish TBS having the composition 94% TBS, 6% TeBS.

EXAMPLES 4–6

Preparation of β-BrBr₃

The precursor β-BrBr₃ is prepared as described in Example 1, but using different solvents and different molar ratios of bromine to phenethyl bromide (β-Br). The reaction conditions and product compositions are set forth in the following table:

TABLE

| β-BrB₄ | β-Br₃ | β-BrBr₂ | Br₂/βBr | Solvent |
|---|---|---|---|---|
| 8 | 92 | — | 3.3 | EDC |
| 4 | 95 | 1 | 3.1 | MC |
| 7 | 92 | 1 | 3.2 | EDB |

Stability Test

The stability of the TBS prepared according to the invention is evidenced by the following test.

A stock of solid TBS monomer, to which 150 ppm of tert-butyl catecol are added as a standard stabilizer for styrenic monomers, is shelf-stored at room temperature.

In each test 8 grs. of TBS taken from this stock are dissolved into 100 ml of acetone. The solution is filtered. Less than 1% of insoluble matter are thus separated. The solution is filtered through a 5μ filter paper, and the amount of polymer formed is determined by gravimetry. It is found to be less than 1%. Without the addition of a stabilizer, the TBS prepared according to the invention would still not polymerize to an extent of more than 1% after several days.

Such a high stability is novel and surprising. Thus the art teaches that DBS is less reactive than TBS, and yet, even when stabilized, it will polymerize in a matter of hours: see e.g. U.S. Pat. No. 4,338,474.

While some embodiments of the invention have been described for purposes of illustration, it will be understood that the invention may be carried into practice by skilled persons with many modifications, variations and adaptations.

We claim:

1. In a process for the preparation of tribromostyrene by the preparation of a tribromostyrene precursor, which is β-bromoethyl-tribromobenzene and the successive elimination of hydrogen bromide from said precursor, which comprises the preparation of said precursor by selective bromination of phenethyl bromide (β-Br), the improvement which comprises:
    (a) that the molar ratio of bromine to phenethyl bromide ranges between 2.5 and 3.5, and preferably between 3.1 and 3.3 inclusive; and
    (b) at least after an amount of bromine ranging between 2 and 3 moles Br₂ per mole of phenethyl bromide has been added, the remaining bromine is added at a controlled molar rate that is not substantially greater than stoichiometrically equivalent to the molar rate of evolution of the hydrogen bromide.

2. Process according to claim 1, wherein after an amount of bromine between 2.5 and 2.7 moles Br₂ per mole of phenethyl bromide have been added, the remaining bromine is added at a controlled molar rate that substantially ranges between 80% and 100% of the molar rate of the evolution of HBr.

3. Process according to claim 1, wherein the selective bromination of phenethyl bromide is further characterized in that an halogenated solvent, non-reactive under the reaction conditions, is added to the reaction mass.

4. Process according to claim 1, wherein the addition of the solvent begins at about the start of the controlled addition of bromine.

5. Process according to claim 3, wherein the halogenated solvent is chosen from among solvents usable in bromination processes.

6. Process according to claim 1, comprising uniformly dispersing the bromine throughout the reaction mass, at least after the start of its controlled addition.

7. Process according to claim 1, comprising maintaining the reaction mass at about room temperature.

8. Process according to claim 1, comprising maintaining the reaction mass at a temperature from about 30° to about 40° C.

9. Process according to claim 3, comprising maintaining the reaction mass under reflux after the beginning of the addition of the solvent.

10. Process according to claim 3, wherein the solvent is added in an amount of at least about 0.5 ml per 1 gr of phenethyl bromide.

11. Process according to claim 1, wherein the phenethyl bromide does not contain, at the start of the reaction, more than 300 ppm of moisture.

12. Process for the preparation of a tribromostyrene precursor, which is β-bromoethyltribromobenzene, by the selective bromination process of claim 1.

13. Process for the preparation of a tribromostyrene precursor, which is β-bromoethyltribromobenzene, by the selective bromination process of claim 2.

14. Process for the preparation of a tribromostyrene precursor, which is β-bromoethyltribromobenzene, by the selective bromination process of claim 3.

15. β-bromoethyl-tribromobenzene which is at least 89% pure and contains less than 5% of β-BrBr₂.

16. Tribromostyrene products, which contain at least 90% of tribromostyrene and are characterized by melting points of at least 60° C. and by high shelf life.

* * * * *